(12) United States Patent
Hashimoto et al.

(10) Patent No.: US 6,646,092 B2
(45) Date of Patent: Nov. 11, 2003

(54) METHOD FOR MANUFACTURING AMPHOTERIC URETHANE RESIN AND AMPHOTERIC URETHANE RESIN AND RESIN COMPOSITION OBTAINED THEREWITH

(75) Inventors: Tomohiro Hashimoto, Kawanishi (JP); Takeshi Baba, Minoo (JP); Seiji Asaoka, Suita (JP); Tetsuo Sakurai, Toyonaka (JP)

(73) Assignee: National Starch and Chemical Investment Holding Corporation, New Castle, DE (US)

( * ) Notice: Subject to any disclaimer, the term of this patent is extended or adjusted under 35 U.S.C. 154(b) by 0 days.

(21) Appl. No.: 10/183,744

(22) Filed: Jun. 26, 2002

(65) Prior Publication Data

US 2003/0088041 A1 May 8, 2003

(30) Foreign Application Priority Data

Jun. 27, 2001 (JP) ........................................ 2001-194865

(51) Int. Cl.[7] .............................................. C08G 18/12
(52) U.S. Cl. ...................... 528/71; 524/731; 525/453; 525/459; 525/460; 525/474
(58) Field of Search ................... 524/731; 525/453, 525/459, 460, 474; 528/71

(56) References Cited

U.S. PATENT DOCUMENTS 6,340,726 B1 * 1/2002 Murray et al.

FOREIGN PATENT DOCUMENTS

| EP | 0 619 111 | 12/1996 |
|---|---|---|
| WO | WO 99/39688 | 8/1999 |
| WO | WO 01/10394 | 2/2001 |
| WO | WO 02/09658 | 2/2002 |

* cited by examiner

*Primary Examiner*—Rachel Gorr
(74) *Attorney, Agent, or Firm*—Karen G. Kaiser

(57) ABSTRACT

The invention presents a method for manufacturing an amphoteric urethane resin, improving at least one of the performance of cosmetics including this amphoteric urethane resin and the storage stability of the urethane resin. The method for manufacturing an amphoteric urethane resin uses (A) a polyol; (B) a polyisocyanate; (C) a polysiloxane compound (except any having at least one selected from a hydroxyl group, a primary amino group and a secondary amino group at one or both ends of the siloxane chain); (D) a compound having carboxyl groups and at least one selected from a hydroxyl group, a primary amino group and a secondary amino group; (E) a compound having tertiary amino groups and at least one selected from a hydroxyl group, a primary amino group and a secondary amino group; and the method includes a step of making a prepolymer including isocyanate groups by reacting the compounds (A), (B) and (D) with excessive isocyanate groups; and a step of reacting the prepolymer including the isocyanate groups with the compound (E); wherein the compound (C) is present in at least one of the first step and the second step.

15 Claims, No Drawings

METHOD FOR MANUFACTURING AMPHOTERIC URETHANE RESIN AND AMPHOTERIC URETHANE RESIN AND RESIN COMPOSITION OBTAINED THEREWITH

BACKGROUND OF THE INVENTION

1. Field of the Invention

The present invention relates to methods for manufacturing amphoteric urethane resins, amphoteric resins obtained with these manufacturing methods, and resin compositions including these amphoteric urethane resins. More specifically, the present invention relates to resin compositions used for cosmetics, to methods for manufacturing amphoteric urethane resins used for such compositions, and to amphoteric urethane resins obtained with such manufacturing methods.

2. Description of the Related Art

Polyurethane resins are superior in flexibility, toughness, and abrasion resistance, and are conventionally used widely as the base in paints for buildings, wood materials and cars, for example. Furthermore, polyurethane resins have also been researched as raw material for cosmetics, and in particular, have been suggested to be useful as raw material for hair fixative.

JP H06-321741 A discloses that using an anionic urethane resin, a hair fixative with excellent hair setting properties, hair texture and hair flaking resistance can be obtained. However, anionic urethane resins have large surface-friction drag, so that in hair fixatives using anionic urethane resins, there is the problem that the touch, the luster, and the washing properties of the hair are poor.

With the object of solving this problem, JP H11-228363A discloses a resin composition for cosmetics, which includes an amphoteric urethane resin having both carboxylic groups and tertiary amino groups in each of its molecules.

Hair fixatives using a resin composition for cosmetics including such an amphoteric urethane resin attain better hair texture and washing abilities than hair fixatives including anionic urethane resins, but evaluating them by more stringent standards, the luster, the touch of the hair, and the spreadability of the hair fixative when applying the hair fixative to hair are insufficient, and a further improvement of its performance is desired. It seems that these problems are caused by the fact that the surface of the amphoteric urethane resins has a large frictional coefficient.

To solve these problems by improving the quality of the amphoteric urethane resin included in the resin composition for cosmetics, JP 2000-192476A discloses a method of introducing polysiloxane chains into the backbone of an amphoteric urethane resin by using a polysiloxane compound having functional groups including active hydrogen at one or both ends of the siloxane chain. On the other hand, JP 2001-48735A proposes a method of adding a polysiloxane compound later to an aqueous solution of an amphoteric urethane resin.

When using a hair fixative with a resin compound for cosmetics including an amphoteric urethane resin in which polysiloxane chains are introduced into the backbone (referred to as a "type 1 amphoteric urethane resin" in the following) by using a polysiloxane compound having functional groups including active hydrogen at one or both ends of the siloxane chain, then the setting properties of the hair are good. However, when using a hair fixative with a resin composition for cosmetics including a type 1 amphoteric urethane resin, the spreadability of the hair fixative is insufficient.

On the other hand, when using a hair fixative with a resin compound for cosmetics including an improved amphoteric urethane resin in which the polysiloxane compound is added later to an aqueous solution of the amphoteric urethane resin (referred to as a "type 2 amphoteric urethane resin" in the following), then the spreadability of the hair fixative is good. However, in type 2 amphoteric urethane resins, the polysiloxane compound added later may separate from the amphoteric urethane resin, so that there is the problem that the storage stability of cosmetics using type 2 amphoteric urethane resins is insufficient.

It is thus an object of the present invention to solve these problems and to provide a method for manufacturing an amphoteric urethane resin, in which at least one selected from the performance of paints, coating agents and cosmetics using the amphoteric urethane resin (in the case of hair fixatives, for example hair setting properties, hair texture, hair washing properties, hair touch and spreadability when applying the hair fixative), and the storage stability of the amphoteric urethane resin is improved compared to conventional amphoteric urethane resins, as well as an amphoteric urethane resin obtained with this manufacturing method and a resin composition including this amphoteric urethane resin.

SUMMARY OF THE INVENTION

In order to achieve these objects, the inventors found as the result of intensive research that by limiting the polysiloxane compound to certain compounds and limiting the time at which this certain polysiloxane compound is added when manufacturing the amphoteric urethane resin, the performance of the resulting amphoteric urethane resin is influenced, and thus conceived of the present invention.

According to one aspect of the present invention, a novel method for manufacturing an amphoteric urethane resin is provided, which uses:

(A) a polyol compound (also referred to as "compound (A)" in the following);

(B) a polyisocyanate compound (also referred to as "compound (B)" in the following);

(C) a polysiloxane compound (except any having at least one selected from a hydroxyl group, a primary amino group and a secondary amino group at one or both ends of the siloxane chain) (also referred to as "compound (C)" in the following);

(D) a compound having carboxyl groups and at least one selected from a hydroxyl group, a primary amino group and a secondary amino group (also referred to as "compound (D)" in the following);

(E) a compound having tertiary amino groups and at least one selected from a hydroxyl group, a primary amino group and a secondary amino group (also referred to as "compound (E)" in the following);

the method including:

a first step of manufacturing a prepolymer including isocyanate groups by reacting the compounds (A), (B) and (D) under the condition of excessive isocyanate groups; and a second step of reacting the prepolymer including the isocyanate groups with the compound (E);

wherein the compound (C) is present in at least one of the first step and the second step.

According to another aspect of the present invention, another method for manufacturing an amphoteric urethane resin is provided,
which uses the compounds (A) to (E);
the method including:
a first step of manufacturing a prepolymer including isocyanate groups by reacting the compounds (A), (B) and (E) under the condition of excessive isocyanate groups; and
a second step of reacting the prepolymer including the isocyanate groups with the compound (D);
wherein the compound (C) is present in at least one of the first step and the second step.

Thus, in the manufacturing methods of the present invention, the order in which the compound (D) and the compound (E) are reacted can be inverted.

One feature of the manufacturing method of the present invention is that the compound (C) is present in at least one of the first step and the second step. Here, the compound (C) can be present at any time during the first step and the second step, and the compound (C) does not necessarily have to be present from the start of the reaction. The compound (C) should be present by the time the reaction product of the second step is mixed with water. Consequently, in this specification, "first step" means the time from the beginning of the reaction of the first step to the beginning of the reaction of the second step, and "second step" means the time from the beginning of the reaction of the second step to the subsequently performed step (more specifically, until the reaction product of the second step explained below is mixed with water).

A feature of the manufacturing method of the present invention is that the compound (C) is "present" in at least one of the first step and the second step. Here, "present" means that the compound (C) is present in the reaction system, and although it is not intended to actively react the compound (C), eventually a portion of the compound (C) may inevitably be reacted. That is to say, the manufacturing method of the present invention, intends to "constrain" the compound (C) with the backbone of the amphoteric urethane resin, or to "entangle" the compound (C) with the backbone of the amphoteric urethane resin, and it does not intend to chemically react the compound (C) actively with the backbone of the amphoteric urethane resin. However, the compound (C) can eventually also form a portion of the backbone of the amphoteric urethane resin, and as long as the desired amphoteric urethane resin can be obtained, this is also included in the manufacturing method of the present invention. Consequently, "amphoteric urethane resin" according to the present invention means an amphoteric urethane resin in which the compound (C) is "constrained by" and/or "entangled with" the backbone of the amphoteric urethane resin, but it can also be an amphoteric urethane resin, in which a portion of the backbone of the amphoteric urethane resin stems from the compound (C). The intention of the present invention is explained in more detail further below.

According to another aspect of the present invention, a novel method for manufacturing an amphoteric urethane resin is provided,
which uses the compounds (A) to (E), and
(F) compound having at least one selected from a hydroxyl group, a primary amino group and a secondary amino group, and structural units indicated by the following formula (11)

Chemical Formula 3

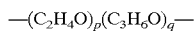

(11)

wherein "p" is an integer of 1 to 500, "q" is an integer of 0 to 400, and
wherein, if the structural units in structural formula (11) are copolymers of $C_2H_4O$ and $C_3H_6O$ (that is, $q \neq 0$), then they can be random copolymers or block copolymers (also referred to as "compound (F)" in the following);
the method comprising:
a first step of manufacturing a prepolymer including isocyanate groups by reacting the compounds (A), (B), (D) and (F) under the condition of excessive isocyanate groups; and
a second step of reacting the prepolymer including the isocyanate groups with the compound (E);
wherein the compound (C) is present in at least one of the first step and the second step.

According to yet another aspect of the present invention, another method for manufacturing an amphoteric urethane resin is provided,
which uses the compounds (A) to (F);
the method comprising:
a first step of manufacturing a prepolymer including isocyanate groups by reacting the compounds (A), (B), (E) and (F) under the condition of excessive isocyanate groups; and
a second step of reacting the prepolymer including the isocyanate groups with the compound (D);
wherein the compound (C) is present in at least one of the first step and the second step.

Thus, in the manufacturing methods of the present invention, the order in which the compound (D) and the compound (E) are reacted can be inverted. Moreover, "present", "first step", and "second step" are as explained above.

In the manufacturing method in accordance with the present invention, it is preferable that after the second step, a chain-extending reaction is performed by mixing the reaction product of the second step with water.

In the manufacturing method in accordance with the present invention, it is also preferable that after the second step, a chain-extending reaction is performed by mixing the reaction product of the second step with alkaline water, or a chain-extending reaction is performed by adding an alkaline compound to the reaction product of the second step, and then mixing it with water.

The present invention also presents an amphoteric urethane resin obtained by the manufacturing method of the present invention, as well as an aqueous solution of such an amphoteric urethane resin and a resin composition including such an amphoteric urethane resin.

The resin composition according to the present invention can be used, for example, as paint for buildings, wood materials and cars, as a coating agent or for cosmetics, but it is particularly useful as a resin composition for cosmetics.

DESCRIPTION OF THE PREFERRED EMBODIMENTS

In this specification, "(A) polyol compound" refers to polyol compounds that are commonly used to manufacture urethane resins, and there is no particular limitation. Examples of such compounds (A) include polyester polyols, polyether polyols, polycarbonate polyols, polybutadiene polyols, polyisoprene polyols, polyolefin polyols, and polyacrylate polyols.

It is particularly preferable to use a polyester polyol or a polyether polyol as the compound (A).

Examples of "polyester polyols" include polyester polyols obtained by condensation polymerization of at least one kind of dicarboxylic acid such as succinic acid, glutaric acid, adipic acid, sebacic acid, azelaic acid, maleic acid, fumaric acid, phthalic acid, and terephthalic acid, and at least one kind of polyhydric alcohol such as ethylene glycol, propylene glycol, 1,4-butanediol, 1,3-butanediol, 1,6-hexadiol, neopentyl glycol, 1,8-octanediol, 1,10-decanediol, diethylene glycol, spiroglycol, and trimethylol propane, as well as polyester polyols obtained by ring-opening polymerization of lactones.

As "polyether polyols", it is possible to use, polyether polyols obtained by ring-opening addition polymerization of water, polyhydric alcohols used for the synthesis of the above-mentioned polyester polyols, phenols such as bisphenol A, their hydrides, or primary amines or secondary amines, with such cyclic ethers as ethylene oxide, propylene oxide, oxetane and tetrahydrofuran. Further examples include polyoxypropylene polyol, polyoxytetramethylene polyol, as well as polyether polyols obtained by ring-opening addition polymerization of at least one of propylene oxide and ethylene oxide with bisphenol A (in case of a copolymer, either a block copolymer or a random copolymer is possible).

Other examples for the compound (A) include LMW polyol compounds, such as 1,4-cyclohexane dimethanol, ethylene glycol, propylene glycol, isopropylene glycol, 1,4-butanediol, 1,3-butanediol, butylene glycol, 1,6-hexadiol, neopentyl glycol, 1,8-octanediol, 1,10-decanediol, diethylene glycol, dipropylene glycol, spiroglycol, trimethylol propane, glycerine, diglycerine, and triglycerine.

It is preferable to use 1,4-cyclohexane dimethanol for the compound (A).

The compound (A) can be used alone or in combination.

Throughout this specification, if a compound of the compounds (A) overlaps with the compounds (F) explained below, then that compound is included in the compounds (F) and not included in the compounds (A).

Also, throughout this specification, if a compound of the compounds (A) overlaps with the compounds (D) explained below, then that compound is included in the compounds (D) and not included in the compounds (A).

And, throughout this specification, if a compound in the compounds (A) overlaps with the compounds (E) explained below, then that compound is included in the compounds (E) and not included in the compounds (A).

"(B) polyisocyanate compound" refers to polyisocyanate compounds that are commonly used to manufacture urethane resins, and there is no particular limitation. Examples of such compounds (B) include organic diisocyanate compounds, such as aliphatic diisocyanate compounds, alicyclic diisocyanate compounds, and aromatic diisocyanate compounds.

Examples of "aliphatic diisocyanate compounds" include ethylene diisocyanate, 2,2,4-trimethylhexamethylene diisocyanate, and 1,6-hexamethylene diisocyanate.

Examples of "alicyclic diisocyanate compounds" include hydrogenated 4,4'-diphenylmethane diisocyanate, 1,4-cyclohexane diisocyanate, methylcyclohexylene diisocyanate, isophorone diisocyanate, and norbornane diisocyanate. Examples of "aromatic diisocyanate compounds" include 4,4'-diphenylmethane diisocyanate, xylylene diisocyanate, toluene diisocyanate, and naphthalene diisocyanate.

1,6-hexamethylene diisocyanate, isophorone diisocyanate, and norbornane diisocyanate are preferable because of their excellent weather resistance and their low cost.

The compound (B) can be used alone or in combination.

"(C) polysiloxane compound (except any having at least one selected from a hydroxyl group, a primary amino group and a secondary amino group at one or both ends of the siloxane chain)" refers to polysiloxane compounds, but not to polysiloxane compounds that have at least one selected from a hydroxyl group (—OH), a primary amino group (—NH$_2$) and a secondary amino group (—NH—) at one or both ends of the siloxane chain, and there is no particular limitation, as long as the desired amphoteric urethane resin can be obtained.

Consequently, the compound (C) includes polysiloxane compounds having at least one selected from a hydroxyl group, a primary amino group and a secondary amino group at portions other than the ends of the siloxane chain (or at a center portion of the siloxane chain), as well as polysiloxane compounds not having any hydroxyl group, primary amino group or secondary amino group at all.

Examples of the compound (C) include at least one selected from polydimethyl siloxane, polyether-modified silicone, cyclic silicone, phenyl-modified silicone, alkyl-modified silicone, and alkoxy-modified silicone.

An example of a "polydimethyl siloxane" is given by the compound illustrated by the general formula (21) below.

Chemical Formula 4

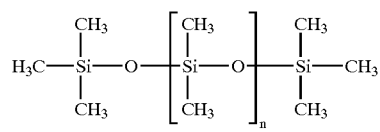

(21)

In formula (21), "n" is an integer of one or greater.

It is preferable that the "n" in formula (21) is an integer of 1 to 100, more preferably an integer of 1 to 50, and most preferably an integer of 3 to 30.

Examples of a "polydimethyl siloxane" include the SH200™ series by Dow Corning Toray Silicone Co., Ltd. and the KF96™ series by Shin-Etsu Chemical Co., Ltd.

An example of a "polyether-modified silicone" is given by the compound illustrated by the general formula (22) below.

Chemical Formula 5

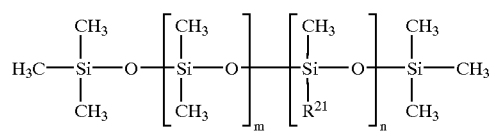

(22)

In formula (22), "m" is an integer of zero or greater and "n" is an integer of one or greater.

R21 is the group illustrated by formula (22-2) below:

Chemical Formula 6

—(CH$_2$)$_a$—(OC$_2$H$_4$)$_b$—(OC$_3$H$_6$)$_c$—OR$^{22}$ (22-2)

In Formula (22-2), R$^{22}$ is a hydrogen atom or a hydrocarbon group with a carbon number of 1 to 10.

"a" is an integer of 1 to 10, "b" is an integer of 1 to 300, and "c" is an integer of 0 to 300.

In formula (22), it is preferable that "m" is an integer of 1 to 300, more preferably an integer of 1 to 100, and most preferably an integer of 1 to 50. "n" is preferably an integer of 1 to 300, more preferably an integer of 1 to 100, and most preferably an integer of 1 to 50.

In formula (22-2), "a" is preferably an integer of 1 to 5, and more preferably an integer of 2 to 4. "b" is preferably an integer of 2 to 50, more preferably an integer of 2 to 40, and most preferably an integer of 2 to 30. "c" is preferably an integer of 0 to 50, more preferably an integer of 0 to 40, and most preferably an integer of 0 to 30.

For the compound (C), it is preferable that in formula 22, "m" is an integer of 1 to 300, "n" is an integer of 1 to 300, $R^{21}$ is the group illustrated by formula (22-2), "a" is an integer of 1 to 5, "b" is an integer of 2 to 50, and "c" is an integer of 0 to 50.

For the compound (C), it is more preferable that in formula 22, "m" is an integer of 1 to 100, "n" is an integer of 1 to 100, $R^{21}$ is the group illustrated by formula (22-2), "a" is an integer of 2 to 4, "b" is an integer of 2 to 40, and "c" is an integer of 0 to 40.

For the compound (C), it is most preferable that in formula 22, "m" is an integer of 1 to 50, "n" is an integer of 1 to 50, $R^{21}$ is the group illustrated by formula (22-2), "a" is an integer of 2 to 4, "b" is an integer of 2 to 30, and "c" is an integer of 0 to 30.

Examples of the compound illustrated by formula (22) include SH3746™, SH3771C™, SH3772C™, SH3773C™, SH3775C™, SH3748™, SH3749™, SH3771M™, SH3772M™, SH3773M™ and SH3775M™ by Dow Corning Toray Silicone Co., Ltd. and KF351A™, KF353A™, KF945A™, KF352A™, KF615A™, KF6011™, KF6012™, KF6013™, KF6015™, KF6016™ and KF6017™ by Shin-Etsu Chemical Co., Ltd.

An example of a "phenyl-modified silicone" is given by the compound illustrated by the general formula (23) below.

Chemical Formula 7

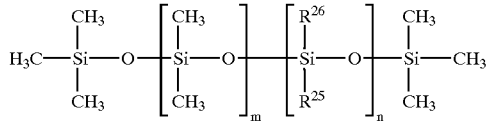

(23)

In formula (23), $R^{25}$ and $R^{26}$ are hydrocarbon groups with a carbon number of 1 to 12 (for example, straight-chained or branched saturated hydrocarbon groups with a carbon number of 1 to 12), —OSi(CH$_3$)$_3$ or phenyl groups, and $R^{25}$ and $R^{26}$ can be the same or different. However, at least one of $R^{25}$ and $R^{26}$ is a phenyl group.

"m" is an integer of zero or greater, and "n" is an integer of one or greater.

In formula (23), it is preferable that "m" is an integer of 0 to 300, more preferably an integer of 0 to 100, and most preferably an integer of 0 to 50. "n" is preferably an integer of 1 to 500, more preferably an integer of 1 to 100, and most preferably an integer of 1 to 50.

For the phenyl-modified silicone, a methylphenyl polysiloxane as in formula (23) with $R^{25}$=CH$_3$ or —OSi(CH$_3$)$_3$, $R^{26}$=C$_6$H$_5$, m=0, n=1 to 100 is particularly preferable.

Examples of phenyl-modified silicones include SH556™, SF557™, SF558™ and SH559™ by Dow Corning Toray Silicone Co., Ltd. and KF50-100cs™, KF50-1000cs™, KF53™, KF54™, and KF56™ by Shin-Etsu Chemical Co., Ltd.

An example of an "alkyl-modified silicone" is given by the compound illustrated by the general formula (24) below.

Chemical Formula 8

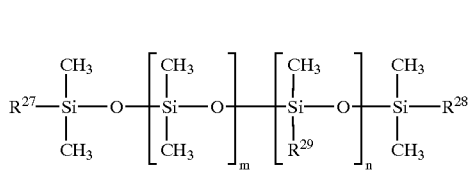

(24)

In formula (24), $R^{27}$ to $R^{29}$ are hydrocarbon groups with a carbon number of 1 to 50, which can be the same or different. However, at least one of $R^{27}$ to $R^{29}$ is a hydrocarbon group with a carbon number of 5 to 30.

"m" is an integer of one or greater, and "n" is an integer of one or greater.

In formula (24), $R^{27}$ to $R^{29}$ are hydrocarbon groups with a carbon number of 1 to 50, for example straight-chained or branched saturated hydrocarbon groups. It is preferable that the hydrocarbon groups have a carbon number of 5 to 30, more preferably of 5 to 20, and most preferably of 10 to 20.

Moreover, "m" is preferably an integer of 1 to 300, more preferably an integer of 1 to 100, and most preferably an integer of 1 to 50. "n" is preferably an integer of 1 to 300, more preferably an integer of 1 to 100, and most preferably an integer of 1 to 50.

Examples of the alkyl-modified silicone include SF8416™ by Dow Corning Toray Silicone Co., Ltd. and KF-412™, KF-413™ and KF-414™ by Shin-Etsu Chemical Co., Ltd.

An example of an "alkoxy-modified silicone" is given by the compound illustrated by the general formula (25) below.

Chemical Formula 9

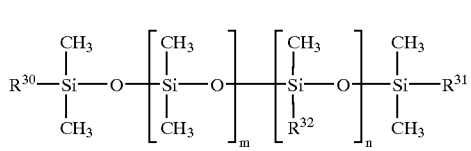

(25)

In formula (25), $R^{30}$ to $R^{32}$ are hydrocarbon groups with a carbon number of 1 to 12, or alkoxy groups with a carbon number of 1 to 50, and $R^{30}$ to $R^{32}$ can be the same or different. However, at least one of $R^{30}$ to $R^{32}$ is an alkoxy group with a carbon number of 1 to 50.

"m" is an integer of zero or greater, and "n" is an integer of one or greater.

In formula (25), $R^{30}$ to $R^{32}$ are hydrocarbon groups with a carbon number of 1 to 12, or alkoxy groups with a carbon number of 1 to 50, and examples of hydrocarbon groups with a carbon number of 1 to 12 include straight-chained and branched saturated hydrocarbon groups, whereas examples of alkoxy groups with a carbon number of 1 to 50 include straight-chained and branched alkoxy groups. The carbon number of the alkoxy groups with a carbon number of 1 to 50 is preferably 1 to 30, more preferably 1 to 25, and most preferably 1 to 20.

"m" is preferably an integer of 1 to 500, more preferably an integer of 1 to 100, and most preferably an integer of 1 to 50. "n" is preferably an integer of 1 to 100, more preferably an integer of 1 to 80, and most preferably an integer of 1 to 50.

Examples of "alkoxy-modified silicones" include KF-851™ and X-22-801™ by Shin-Etsu Chemical Co., Ltd.

An example of a "cyclic silicone" is given by the compound illustrated by the general formula (26).

Chemical Formula 10

(26)

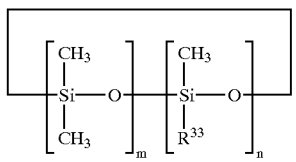

In formula (26), $R^{33}$ denotes a hydrocarbon group with a carbon number of 2 to 12, wherein the repeating units can be the same or different "m" is an integer of one or greater, and "n" is an integer of zero or greater, and the sum of "m" and "n" (m+n) is 3 to 10.

In formula (26), $R^{33}$ is a hydrocarbon group with a carbon number of 2 to 12, for example a straight-chained or branched saturated hydrocarbon group. $R^{33}$ has a carbon number of preferably 2 to 10, more preferably of 2 to 8, and most preferably of 2 to 5.

"m" is preferably an integer of 3 to 8, more preferably an integer of 4 to 8, and most preferably an integer of 4 to 6. "n" is preferably an integer of 0 to 7, more preferably an integer of 0 to 5, and most preferably an integer of 0 to 3. The sum of "m" and "n" (m+n) is preferably 3 to 8, more preferably 4 to 8 and most preferably 4 to 6.

Examples of cyclic silicones include SH244™, SH344™, SH245™, DC345™ and DC246™ by Dow Corning Toray Silicone Co., Ltd. and KF994™, KF995™ and KF9937™ by Shin-Etsu Chemical Co., Ltd.

The repeating units in the compounds shown in the formulas (22) to (26) can be of any polymer type, such as random polymers or block polymers.

The viscosity (dynamic viscosity) of the compound (C) at 25° C. is preferably 1 to 5000 mm$^2$/s, more preferably 1 to 2000 mm$^2$/s, and most preferably 1 to 1000 mm$^2$/s.

For the compound (C), polydimethyl siloxanes and polyether-modified silicones are preferable.

The compound (C) can be used alone or in combination. "(D) compound having carboxyl groups and at least one selected from a hydroxyl group, a primary amino group and a secondary amino group" refers to a compound containing at least one selected from a hydroxyl group, a primary amino group and a secondary amino group, and at least one carboxyl group in its molecules, and there is no particular limitation, as long as the desired amphoteric urethane resin can be obtained with that compound.

Examples of the compound (D) include dimethylolpropanoic acid, dimethylolbutanoic acid, and polycaprolactone diol including carboxylic groups.

The compound (D) can be used alone or in combination.

"(E) compound having tertiary amino groups, and at least one selected from a hydroxyl group, a primary amino group and a secondary amino group" refers to a compound containing at least one selected from a hydroxyl group, a primary amino group and a secondary amino group, and at least one tertiary amino group in its molecules, and there is no particular limitation, as long as the desired amphoteric urethane resin can be obtained with that compound.

Examples of the compound (E) include N-alkyldialkanolamine compounds, such as N-methyldiethanolamine, N-ethyldiethanolamine, N-butyldiethanolamine, N-lauryldiethanolamine, N-methyldipropanolamine, and N,N-dialkylalkanolamine compounds, such as N,N-dimethylethanolamine, N,N-diethylethanolamine, N,N-dibutylethanolamine, as well as triethanolamines.

The compound (E) can be used alone or in combination.

It is preferable that the weight ratio of the compound (C) to the compounds (A), (B), (D) and (E), i.e. (C)/((A)+(B)+(D)+(E)) is 0.1/100 to 30/100, more preferably 0.5/100 to 25/100, and most preferably 1/100 to 20/100.

Moreover, the mole ratio of compound (B) to compounds (A), (D) and (E), i.e. (B)/((A)+(D)+(E)) is preferably 2.0/0.8 to 2.0/1.8, more preferably 2.0/1.0 to 2.0/1.8, and most preferably 2.0/1.2 to 2.0/1.8.

A method for manufacturing an amphoteric urethane resin in accordance with the present invention includes:

a first step of manufacturing a prepolymer including isocyanate groups by reacting the above-described compounds (A), (B) and (D) under the condition of excessive isocyanate groups, and a second step of reacting the prepolymer including the isocyanate groups with the compound (E), wherein the compound (C) is present in at least one of the first step and the second step.

In another method for manufacturing the amphoteric urethane resin according to the present invention, the order in which the compound (E) and the compound (D) are reacted is inverted.

The reactions of the first step and the second step can be carried out with suitable polymerization catalysts and under reaction conditions that are ordinarily used to manufacture polyurethanes.

As a "polymerization catalyst", it is possible to use any polymerization catalyst that is ordinarily used to manufacture urethane resins. There is no particular limitation with regard to the polymerization catalyst, as long as the desired amphoteric urethane resin can be obtained. It is possible to use, for example, a tertiary amine catalyst or an organic metal catalyst for the "polymerization catalyst". Examples of "tertiary amines" include [2,2,2]-diazabicyclooctane (DABCO), tetramethylenediamine, N-methylmorpholine, and diazabicycloundecene (DBU). Examples of "organic metal catalysts" include dibutyltindilaurate.

In all of the manufacturing methods of the present invention, an organic solvent can be used as necessary for the reactions of the first step and the second step. It is particularly preferable to use an organic solvent that can dissolve the compounds (A) to (E) as well as the urethane resin to be created. Examples of such an organic solvent include amides, such as N-methyl-pyrolidine, dimethylformamide, and dimethylacetoamide, ketones, such as acetone, and methylethylketone, esters, such as ethyl acetate, and cellosolve acetate or cellosolve ether.

Furthermore, in the manufacturing methods according to the present invention, it is preferable to mix, after the second step, the reaction product of the second step with water to carry out a chain-extending reaction.

In the manufacturing methods according to the present invention, it is preferable that, after the second step, the chain-extending reaction is performed by mixing the reaction product of the second step with alkaline water, or by adding an alkaline compound to the reaction product of the second step and then mixing it with water. It is more preferably to perform the chain-extending reaction by mixing the reaction product of the second step with alkaline water.

Here, "alkaline water" refers to water, in which an alkaline substance has been dissolved, so that the water has alkalinity. Examples of alkaline water include water in which, for example, triethylamine, triethanolamine, ammonia, sodium hydroxide, potassium hydroxide or 2-amino-2-methyl-1-propanol has been dissolved.

It is preferable to perform a chain-extending reaction in the manufacturing method of the present invention. In the chain-extending reaction, it is possible to use a chain-extending agent, and it is possible to adjust the properties of the finally obtained amphoteric urethane resin with this chain-extending reaction.

A "chain-extending agent" is a compound that is used for a chain-extending reaction. Examples of chain-extending agents include LMW polyols, amines and water. Examples of LMW polyols include glycols, such as ethylene glycol, propylene glycol, 1,4-butanediol, diethylene glycol, 1,6-hexadiol, spiroglycol, bis(P-hydroxyethoxy)benzene, and xylylene glycol, as well as triols, such as trimethylolpropane and glycerin. Examples of "amines" include methylene(bis-o-chloraniline).

In the method for manufacturing an amphoteric urethane resin in accordance with the present invention, it is preferable that, after the second step, the reaction product of the second step is mixed with alkaline water to perform a chain-extending reaction in water.

Furthermore, in the method for manufacturing an amphoteric urethane resin in accordance with the present invention, it is preferable that, after the reactions of the first step and the second step have been performed in an organic solvent, the reaction mixture after the second step is mixed with alkaline water, and subsequently the chain-extending reaction is performed in the water.

This configuration of mixing the reaction mixture after the second step with alkaline water, and subsequently performing the chain-extending reaction in water is preferable, because this way, an amphoteric urethane resin of high molecular weight can be obtained easily. In the manufacturing method of this configuration, it is preferable that the manufacturing conditions are set such that the reaction mixture after the second step is a prepolymer including isocyanate groups at its chain ends.

In the manufacturing method of the present invention, a manufacturing method is presented, which uses, in addition to the compounds (A) to (E), "(F) compound having at least one selected from a hydroxyl group, a primary amino group and a secondary amino group, and structural units indicated by the following formula (11)

Chemical Formula 11

  (11)

wherein "p" is an integer of 1 to 500, "q" is an integer of 0 to 400, and if the structural units in formula (11) are copolymers of $C_2H_4O$ and $C_3H_6O$ (that is $q \neq 0$), then they can be random copolymers or block copolymers (referred to as "compound (F)" in the following).

The compound (F) is a compound having "at least one selected from a hydroxyl group, a primary amino group and a secondary amino group, and structural units indicated by the formula (11)", and there is no limitation with regard to the compound (F), as long as the desired amphoteric urethane resin can be obtained.

If in the formula (11) q=0, then the structural units shown by the formula (11) forms a $C_2H_4$ polymer (polyoxyethylene), and if $q \neq 0$, then they form a copolymer of $C_3H_6O$ and $C_2H_4O$. In the case of copolymers of $C_3H_6O$ and $C_2H_4O$, the structural units shown in formula (11) can be random copolymers or block copolymers, and are not limited by the arrangement of $C_2H_4O$ and $C_3H_6O$.

In formula (11), regardless whether $q \neq 0$ or q=0, "p" is preferably 3 to 250, more preferably 3 to 120, and most preferably 3 to 50.

If "p" is less than 3, then the compound (F) does not contain enough $C_2H_4O$ and it may be difficult to provide the amphoteric urethane resin with enough hydrophilicity. Consequently, if the amphoteric urethane resin is used as hair fixative, the hydrophilicity and hair-washing properties of the hair fixative may be insufficient. If "p" is larger than 500, then the compound (F) contains too much $C_2H_4O$, so that the amphoteric urethane resin is provided with too much hydrophilicity. Consequently, the hydrophilicity of the hair fixative may be too strong, and if the amphoteric urethane resin is used as hair fixative, the moisture resistance of the hair may decrease.

If in formula (11) $q \neq 0$, then "q" is preferably 3 to 200, more preferably 3 to 100, and most preferably 3 to 40.

In formula (11), regardless whether $q \neq 0$ or q=0, p+q is preferably 3 to 300, more preferably 10 to 120, and most preferably 3 to 50.

In formula (11), regardless whether $q \neq 0$ or q=0, the weight ratio between $C_2H_4O$ and $C_3H_6O$ (i.e. $C_2H_4O/C_3H_6O$) is preferably 10/0 to 2/8 more preferably 10/0 to 3/7, and most preferably 10/0 to 4/6.

Regarding the structural units shown by formula (11), it is preferable that q=0.

It is preferable that the compound (F) is of the type with OH groups introduced at both ends, the type with $NH_2$ groups introduced at both ends, the type with an OH group introduced at one end, or of the type with an $NH_2$ group introduced at one end. If a compound (F) of the type with OH groups introduced at both ends or the type with $NH_2$ groups introduced at both ends is used, then an amphoteric urethane resin is obtained, that has the structural units shown in formula (11) within the principal chain. If a compound (F) of the type with an OH group introduced at one end or of the type with an $NH_2$ group introduced at one end is used, then an amphoteric urethane resin is obtained, that has the structural units shown in formula (11) in a side chain or at the chain end.

The weight-average molecular weight of the compound (F) is preferably 200 to 20000, more preferably 200 to 5000, and most preferably 500 to 2000.

Examples of the compound (F) include polyethyleneglycol (PEG) and polyethylene-polypropylene glycol (polyethylene-polypropylene block copolymer), but polyethyleneglycol (or polyoxyethylene polyol) is preferable.

The compound (F) can be used alone or in combination.

Consequently, the present invention provides a method for manufacturing an amphoteric urethane resin, including a first step of manufacturing a prepolymer including isocyanate groups by reacting the compounds (A), (B), (D) and (F) under the condition of excessive isocyanate groups, and a second step of reacting the prepolymer including the isocyanate groups with the compound (E), wherein the compound (C) is present in at least one of the first step and the second step.

The present invention also provides a method for manufacturing an amphoteric urethane resin, including a first step of manufacturing a prepolymer including isocyanate groups by reacting the compounds (A), (B), (E) and (F) under the condition of excessive isocyanate groups, and a second step of reacting the prepolymer including the isocyanate groups with the compound (D), wherein the compound (C) is present in at least one of the first step and the second step.

The reactions of the first step and the second step to which the compound (F) has been added can be carried out similarly as the afore-mentioned first and second step, can be carried out with suitable polymerization catalysts and under reaction conditions that are ordinarily used to manufacture polyurethanes.

The "polymerization catalyst", "organic solvent", "chain-extending agent" etc. can be as described above, and when the compound (F) is added, it is preferable that the first step and the second step are carried out in an organic solvent, and the chain-extending reaction is carried out in water.

The weight ratio of the compound (C) and the compounds (A), (B), and (D) to (F), i.e. (C)/((A)+(B)+(D)+(E)+(F)) is preferably 0.1/100 to 30/100, more preferably 0.5/100 to 25/00, and most preferably 1/100 to 20/100.

The mole ratio of the compound (B) and the compounds (A), (D), (E) and (F), i.e. (B)/((A)+(D)+(E)+(F)) is preferably 2.0/0.8 to 2.0/1.8, more preferably 2.0/1.0 to 2.0/1.8, and most preferably 2.0/1.2 to 2.0/1.8.

The present invention provides an amphoteric urethane resin that is obtained by the above-described manufacturing methods.

The amphoteric urethane resin obtained with the manufacturing methods according to the present invention has carboxylic groups and tertiary amino groups in each molecule. The ratio between carboxylic groups and tertiary amino groups (the ratio between the number of both functional groups), i.e. carboxylic groups/tertiary amino groups, is preferably 1/50 to 50/1, more preferably 1/1 to 50/1, and most preferably 1/1 to 25/1. If the ratio between carboxylic groups and tertiary amino groups in the amphoteric urethane resin is 1/50 to 50/1, then the hair can be provided with a more pleasant texture when using it for a hair fixative with a resin composition including an amphoteric urethane resin, or in the case of a paint or coating with a resin composition including the amphoteric urethane resin, better adhesion to the substrate can be attained.

In the manufacturing method of the present invention, the ratio (mole ratio) between the compounds (D) and (E), i.e. compound (D)/compound (E), is preferably 1/50 to 50/1, more preferably 1/1 to 50/1, and most preferably 1/1 to 25/1.

The amphoteric urethane resin according to the present invention is preferably used in form of an aqueous solution, and it is preferable that the amphoteric urethane resin according to the present invention forms an aqueous solution when mixed with water. In this specification "aqueous solution" refers not only to aqueous solutions in which the amphoteric urethane resin is completely dissolved in water, but also to aqueous dispersions and/or aqueous suspensions in which the amphoteric urethane resin is dispersed and/or suspended in water. The present invention provides an aqueous solution of the amphoteric urethane resin according to the present invention.

However, it is also possible to use the resin component of the amphoteric urethane resin obtained by practically eliminating the solvent.

In this specification, "water" means any kind of water, and includes distilled water, ion exchanged water, and pure water. Furthermore, within a range that does not adversely affect the manufacturing and the quality of the desired amphoteric urethane resin, the "water" can also include organic solvents, monomers, etc. that are soluble or dispersible in water.

The present invention presents a resin composition including the above-described amphoteric urethane resin.

Here, "resin composition" means compositions including various additives that are commonly added to urethane resins. Examples of such "additives" include pigments, dyes, coloring agents, perfumes, surfactants, moisturizing agents, preservatives, disinfectants, antiseptics, antioxidants, thickeners, and pH-adjusting agents. It is preferable that also the "resin composition" is used in form of an aqueous solution. Needless to say, it is also possible to subject the "resin composition" to additional processing, such as adding other additives, and, depending on its purpose, subject it to other modifications, as suitable.

The "amphoteric urethane resin" and the "resin composition including an amphoteric urethane resin" according to the present invention can be used for any field in which urethane resins are ordinarily used, such as cosmetics, paints, and coating agents, for example. It is preferable to use them for cosmetics. Examples of "cosmetics" include hair fixatives, coating agents, and viscosity modifiers. Examples of "hair fixatives" include hair fixatives in form of foams, gels, aerosol sprays, and pump sprays. Examples of "coating agents" and "viscosity modifiers" include conditioning/shaving/creaming agents, skin care lotions, emulsified foundations, cream foundations, eyeliners, mascaras, nail color, and packs.

With the amphoteric urethane resin according to the present invention, at least one effect selected from improving the performance of paints, coating agents and cosmetics using the amphoteric urethane resin according to the present invention and improving the storage stability of the amphoteric urethane resin compared to conventional amphoteric urethane resins is achieved, and it is particularly superior in cosmetics. This seems to be due to the following reasons.

The amphoteric urethane resin according to the present invention does not necessarily include polysiloxane chains of the polysiloxane compound (C) through covalent bonds in its backbone, and it seems that the amphoteric urethane resin includes polysiloxane chains by entangling its backbone physically with the polysiloxane chains of the polysiloxane compound (C). This mutual entanglement is further complicated by the proceeding polymerization reaction of the amphoteric urethane, and it seems to be difficult to separate the polysiloxane compounds from the obtained amphoteric urethane resin.

In this specification, the entanglement of the backbone of the amphoteric urethane resin and the polysiloxane compounds is referred to as a state in which the backbone of the amphoteric urethane resin "constrains" the polysiloxane compounds. Here, "constraint" differs depending on whether the amphoteric urethane resin is in form of an aqueous solution or in form of an aqueous dispersion. The backbone of the amphoteric urethane resin has usually a straight-chain structure, but it can also have a branched structure or a cross-linked structure. If the amphoteric urethane resin is in form of an "aqueous solution", then it seems that polysiloxane chains enter the backbone of the amphoteric urethane resin.

On the other hand, if the amphoteric urethane resin is in the form of an "aqueous dispersion", then it seems that the amphoteric urethane resin has the form of particles dispersed in water, and several forms are conceivable for the "constraint" of the particles with respect to the polysiloxane chains. In a first form, all or some of the polysiloxane chains are bundled inside the particles. In a second form, the ends of the polysiloxane chains are bundled inside the particles. In a third form, the polysiloxane chains are attached to the surface of the particles. The first to third forms all correspond to "constraints", and also any mixture of the first to third forms corresponds to a constraint.

The backbone of the amphoteric urethane resin according to the present invention seems to constrain the polysiloxane compound (C). Therefore, while the polysiloxane chains have the quality of being relatively mobile, it seems that the polysiloxane compounds are relatively hard to separate from the amphoteric urethane resin. Consequently, at least one effect selected from improving the performance of paints, coating agents and cosmetics using the amphoteric urethane resin according to the present invention (for example, in the case of hair fixatives, properties such as the hair setting properties, the hair texture, the hair washing properties, and the hair touch, as well as the spreadability when applying the hair fixative) and improving the storage stability of the amphoteric urethane resin compared to conventional amphoteric urethane resins is achieved, and it is particularly superior in cosmetics.

It should be noted that the superior quality of the amphoteric urethane resin of the present invention is apparently due to these reasons, but the amphoteric urethane resin of the present invention is in no way limited by these reasons.

WORKING EXAMPLES

The following is a more detailed description of the present invention by way of working examples and comparative examples. However, these working examples are only some of the possible embodiments of the present invention, and the present invention is by no means limited to these working examples.

(1) Manufacture of Amphoteric Urethane Resin Aqueous Solutions of the Working Examples and the Comparative Examples Manufacture of Amphoteric Urethane Resin Aqueous Solution of Working Example 1

70 g isophorone diisocyanate (IPDI), 63 g polypropylene glycol (PPG; weight-average molecular weight: 1000), 7 g 1,4-cyclohexyane dimethanol (CHDM), 8 g polydimethylsiloxane (with a viscosity of 10 $mm^2/s$ at 25° C.; SH200C-10cs™ by Dow Corning Toray Silicone Co., Ltd.), and 20 g dimethylolbutanoic acid (DMBA) were given into a four-necked flask equipped with an agitator, a thermometer, a nitrogen inlet tube, and a reflux condenser. 50 g ethyl acetate were added as a solvent, and heating to 80° C. with an oil bath, the mixture was reacted for three hours. Then, 2 g N-methyldiethanolamine (NMDEtA) and 60 g ethyl acetate were added, the reaction was carried out a further three hours at 80° C., and a prepolymer with remaining isocyanate groups was obtained. After cooling down the prepolymer with remaining isocyanate groups to 50° C., it was dispersed by high-speed agitation in 700 g water including 10 g potassium hydroxide, and a chain-extending reaction was performed for three hours at 50° C., thereby achieving high molecular weight. The ethyl acetate was recovered from the resulting aqueous solution, and an amphoteric urethane resin aqueous solution of the Working Example 1, which contained substantially no solvent, was obtained.

Manufacture of Amphoteric Urethane Resin Aqueous Solution of Working Example 2

The amphoteric urethane resin aqueous solution of the Working Example 2 was obtained in the same manner as in the manufacturing method of the Working Example 1, except that 8 g polyether-modified silicone (with a viscosity of 1600 $mm^2/s$ at 25° C.; SH3775C™ by Dow Corning Toray Silicone Co., Ltd.) were used instead of the 8 g polydimethylsiloxane.

Manufacture of Amphoteric Urethane Resin Aqueous Solution of Working Example 3

The amphoteric urethane resin aqueous solution of the Working Example 3 was obtained in the same manner as in the manufacturing method of the Working Example 1, except that 8 g cyclic silicone (with a viscosity of 4 $mm^2/s$ at 25° C.; SH245™ by Dow Corning Toray Silicone Co., Ltd.) were used instead of the 8 g polydimethylsiloxane.

Manufacture of Amphoteric Urethane Resin Aqueous Solution of Working Example 4

The amphoteric urethane resin aqueous solution of the Working Example 4 was obtained in the same manner as in the manufacturing method of the Working Example 1, except that 8 g phenyl-modified silicone (with a viscosity of 22 $mm^2/s$ at 25° C.; SH556™ by Dow Corning Toray Silicone Co., Ltd.) were used instead of the 8 g polydimethylsiloxane.

Manufacture of Amphoteric Urethane Resin Aqueous Solution of Working Example 5

The amphoteric urethane resin aqueous solution of the Working Example 5 was obtained in the same manner as in the manufacturing method of the Working Example 1, except that 8 g alkyl-modified silicone (with a viscosity of 500 $mm^2/s$ at 25° C.; KF-412™ by Shin-Etsu Chemical Co., Ltd.) were used instead of the 8 g polydimethylsiloxane.

Manufacture of Amphoteric Urethane Resin Aqueous Solution of Working Example 6

The amphoteric urethane resin aqueous solution of the Working Example 6 was obtained in the same manner as in the manufacturing method of the Working Example 1, except that 8 g alkoxy-modified silicone (with a viscosity of 80 $mm^2/s$ at 25° C.; KF-851™ by Shin-Etsu Chemical Co., Ltd.) were used instead of the 8 g polydimethylsiloxane.

Manufacture of Amphoteric Urethane Resin Aqueous Solution of Working Example 7

The amphoteric urethane resin aqueous solution of the Working Example 7 was obtained in the same manner as in the manufacturing method of the Working Example 1, except that 20 g polydimethylsiloxane (with a viscosity of 10 $mm^2/s$ at 25° C.; SH200C-10cs™ by Dow Corning Toray Silicone Co., Ltd.) were used instead of the 8 g polydimethylsiloxane.

Manufacture of Amphoteric Urethane Resin Aqueous Solution of Working Example 8

The amphoteric urethane resin aqueous solution of the Working Example 8 was obtained in the same manner as in the manufacturing method of the Working Example 1, except that 20 g polyether-modified silicone (with a viscosity of 1600 $mm^2/s$ at 25° C.; SH3775C™ by Dow Corning Toray Silicone Co., Ltd.) were used instead of the 8 g polydimethylsiloxane.

Manufacture of Amphoteric Urethane Resin Aqueous Solution of Working Example 9

70 g isophorone diisocyanate (IPDI), 55 g polypropylene glycol (PPG; weight-average molecular weight: 1000), 8 g polyethylene glycol (PEG; weight-average molecular weight: 1000), 7 g 1,4-cyclohexyane dimethanol (CHDM), 8 g polydimethylsiloxane (with a viscosity of 10 $mm^2/s$ at 25° C.; SH200C-10cs™ by Dow Corning Toray Silicone Co., Ltd.), and 20 g dimethylolbutanoic acid (DMBA) were given into a four-necked flask equipped with an agitator, a thermometer, a nitrogen inlet tube, and a reflux condenser. 50 g ethyl acetate were added as a solvent, and heating to 80° C. with an oil bath, the mixture was reacted for three hours. Then, 2 g N-methyldiethanolamine (NMDEtA) and 60 g ethyl acetate were added, the reaction was carried out a further three hours at 80° C., and a prepolymer with remaining isocyanate groups was obtained. After cooling down the prepolymer with remaining isocyanate groups to 50° C., it was dispersed by high-speed agitation in 700 g water including 10 g potassium hydroxide, and a chain-extending reaction was performed for three hours at 50° C., thereby achieving high molecular weight. The ethyl acetate was recovered from the resulting aqueous solution, and the amphoteric urethane resin aqueous solution of the Working Example 9, which contained substantially no solvent, was obtained.

Manufacture of Amphoteric Urethane Resin Aqueous Solution of Working Example 10

The amphoteric urethane resin aqueous solution of the Working Example 10 was obtained in the same manner as in the manufacturing method of the Working Example 9, except that 8 g polyether-modified silicone (with a viscosity of 1600 mm$^2$/s at 25° C.; SH3775C™ by Dow Corning Toray Silicone Co., Ltd.) were used instead of the 8 g polydimethylsiloxane.

Manufacture of Amphoteric Urethane Resin Aqueous Solution of Working Example 11

The amphoteric urethane resin aqueous solution of the Working Example 11 was obtained in the same manner as in the manufacturing method of the Working Example 9, except that 20 g polydimethylsiloxane (with a viscosity of 10 mm$^2$/s at 25° C.; SH200C-10cs™ by Dow Corning Toray Silicone Co., Ltd.) were used instead of the 8 g polydimethylsiloxane.

Manufacture of Amphoteric Urethane Resin Aqueous Solution of Working Example 12

The amphoteric urethane resin aqueous solution of the Working Example 12 was obtained in the same manner as in the manufacturing method of the Working Example 9, except that 20 g polyether-modified silicone (with a viscosity of 1600 mm$^2$/s at 25° C.; SH3775C™ by Dow Corning Toray Silicone Co., Ltd.) were used instead of the 8 g polydimethylsiloxane.

Manufacture of Amphoteric Urethane Resin Aqueous Solution of Comparative Example 1

The amphoteric urethane resin aqueous solution of the Comparative Example 1 was obtained in the same manner as in the manufacturing method of the Working Example 1, except that no polydimethylsiloxane was used at all.

Manufacture of Amphoteric Urethane Resin Aqueous Solution of Comparative Example 2

70 g isophorone diisocyanate (IPDI), 63 g polypropylene glycol (PPG; weight-average molecular weight: 1000), 7 g 1,4-cyclohexyane dimethanol (CHDM), and 20 g dimethylolbutanoic acid (DMBA) were given into a four-necked flask equipped with an agitator, a thermometer, a nitrogen inlet tube, and a reflux condenser. 50 g ethyl acetate were added as a solvent, and heating to 80° C. with an oil bath, the mixture was reacted for three hours. Then, 2 g N-methyldiethanolamine (NMDEtA) and 60 g ethyl acetate were added, the reaction was carried out a further three hours at 80° C., and a prepolymer with remaining isocyanate groups was obtained. After cooling down the prepolymer with remaining isocyanate groups to 50° C., it was dispersed by high-speed agitation in 700 g water including 10 g potassium hydroxide, and a chain-extending reaction was performed for three hours at 50° C., thereby achieving high molecular weight. The ethyl acetate was recovered from the resulting aqueous solution, and after obtaining an aqueous solution of amphoteric urethane resin containing substantially no solvent was obtained, 8 g polydimethylsiloxane (with a viscosity of 10 mm$^2$/s at 25° C.; SH200C-10cs™ by Dow Corning Toray Silicone Co., Ltd.) were added to obtain the amphoteric urethane resin aqueous solution of the Comparative Example 2.

Manufacture of Amphoteric Urethane Resin Aqueous Solution of Comparative Example 3

The amphoteric urethane resin aqueous solution of the Comparative Example 3 was obtained in the same manner as in the manufacturing method of the Comparative Example 2, except that 8 g polyether-modified silicone (with a viscosity of 1600 mm$^2$/s at 25° C.; SH3775C™ by Dow Corning Toray Silicone Co., Ltd.) were used instead of the 8 g polydimethylsiloxane.

Manufacture of Amphoteric Urethane Resin Aqueous Solution of Comparative Example 4

The amphoteric urethane resin aqueous solution of the Comparative Example 4 was obtained in the same manner as in the manufacturing method of the Comparative Example 2, except that 8 g cyclic silicone (with a viscosity of 4 mm$^2$/s at 25° C.; SH245™ by Dow Corning Toray Silicone Co., Ltd.) were used instead of the 8 g polydimethylsiloxane.

Manufacture of Amphoteric Urethane Resin Aqueous Solution of Comparative Example 5

The amphoteric urethane resin aqueous solution of the Comparative Example 5 was obtained in the same manner as in the manufacturing method of the Comparative Example 2, except that 8 g phenyl-modified silicone (with a viscosity of 22 mm$^2$/s at 25° C.; SH556™ by Dow Corning Toray Silicone Co., Ltd.) were used instead of the 8 g polydimethylsiloxane.

Manufacture of Amphoteric Urethane Resin Aqueous Solution of Comparative Example 6

The amphoteric urethane resin aqueous solution of the Comparative Example 6 was obtained in the same manner as in the manufacturing method of the Comparative Example 2, except that 8 g alkyl-modified silicone (with a viscosity of 500 mm$^2$/s at 25° C.; KF-412™ by Shin-Etsu Chemical Co., Ltd.) were used instead of the 8 g polydimethylsiloxane.

Manufacture of Amphoteric Urethane Resin Aqueous Solution of Comparative Example 7

The amphoteric urethane resin aqueous solution of the Comparative Example 7 was obtained in the same manner as in the manufacturing method of the Comparative Example 2, except that 8 g alkoxy-modified silicone (with a viscosity of 80 mm$^2$/s at 25° C.; KF-851™ by Shin-Etsu Chemical Co., Ltd.) were used instead of the 8 g polydimethylsiloxane.

Manufacture of Amphoteric Urethane Resin
Aqueous Solution of Comparative Example 8

The amphoteric urethane resin aqueous solution of the Comparative Example 8 was obtained in the same manner as in the manufacturing method of the Working Example 1, except that 8 g polydimethylsiloxanediol (of the type with OH groups introduced at both ends; with a viscosity of 62 mm$^2$/s at 25° C.; KF-6002™ by Shin-Etsu Chemical Co., Ltd.) were used instead of the 8 g polydimethylsiloxane, and 55 g polypropylene glycol (PPG; weight-average molecular weight: 1000) were used instead of the 63 g polypropylene glycol (PPG; weight-average molecular weight: 1000).

Manufacture of Amphoteric Urethane Resin
Aqueous Solution of Comparative Example 9

The amphoteric urethane resin aqueous solution of the Comparative Example 9 was obtained in the same manner as in the manufacturing method of the Working Example 1, except that 8 g polydimethylsiloxanediol (of the type with an OH group introduced at one end; with a viscosity of 88 mm$^2$/s at 25° C.; X-22-176B™ by Shin-Etsu Chemical Co., Ltd.) were used instead of the 8 g polydimethylsiloxane, and 55 g polypropylene glycol (PPG; weight-average molecular weight: 1000) were used instead of the 63 g polypropylene glycol (PPG; weight-average molecular weight: 1000).

(2) Evaluation of the Amphoteric Urethane Resin Aqueous Solutions of the Working Examples and the Comparative Examples Evaluation Used for Hair Fixative Foams To evaluate the amphoteric urethane resin aqueous solutions of the working examples and the comparative examples obtained as explained above, hair fixatives foam of the working examples and the comparative examples were prepared with each of the amphoteric urethane resin aqueous solutions.

That is to say, the components shown in Table 1 were mixed at the proportions shown in that table, and stirred until uniform, thus obtaining the X component for the working examples and comparative examples. Then, the Y component in Table 1 was added to the X component at the proportions shown in that table, thus preparing hair fixative foams according to each of the working examples and comparative examples. These are referred to as the hair fixative foams of the Working Examples 1 to 12 and the hair fixative foams of the Comparative Examples 1 to 9.

TABLE 1

| hair fixative foams of working and comp. examples | | weight % |
|---|---|---|
| X component | amphoteric urethane resin aqueous solution of working and comp. examples | 2.5[a] |
| | deionized water | 78.5 |
| | polyoxyethylenelaurylether | 0.5 |
| | coconut oil fatty acid diethanolamide | 0.5 |
| | ethanol | 10.0 |
| Y component | propellant | 8.0 |

[a])Dry weight. Weight of residue remaining after heating the solution to 105° C. for three hours.

Using the hair fixative foam of the working examples and comparative examples obtained in this manner, the hair setting properties (also referred to as "setting properties" in the following), the hair texture (also referred to as "texture" in the following), the hair washing properties (also referred to as "hair washing properties" in the following), the hair touch (also referred to as "touch" in the following), and the spreadability of the hair fixative (also referred to as "spreadability" in the following) were evaluated. Furthermore, the storage stability of the amphoteric urethane resin aqueous solutions of the working examples and the comparative examples were evaluated. The results are listed in Tables 2 and 3.

Setting Properties 0.8 g of each of the hair fixative foams were applied to a bundle of black virgin hair (length: 25 cm long; weight: 5.0 g), and dried at room temperature to prepare hair bundles for the evaluation of the setting properties. These hair bundles were subjected to a sensory test with ten testers, who evaluated their setting properties. The evaluation criteria with regard to the setting properties were as follows:

"A" means that the setting properties of the hair bundle were evaluated as very good by at least nine testers;
"B" means that the setting properties of the hair bundle were evaluated as very good by six to eight testers;
"C" means that the setting properties of the hair bundle were evaluated as very good by two to five testers; and
"D" means that the setting properties of the hair bundle were evaluated as very good by one or none of the testers.

Texture 0.8 g of each of the hair fixative foams were applied to a bundle of black virgin hair (length: 25 cm long; weight: 5.0 g), and dried at room temperature to prepare hair bundles for the evaluation of the texture. These hair bundles were subjected to a sensory test with ten testers, who evaluated their texture. The evaluation criteria with regard to texture were as follows:

"A" means that at least nine testers evaluated the feeling of the hair bundle as very supple;
"B" means that six to eight testers evaluated the feeling of the hair bundle as very supple;
"C" means that two to five testers evaluated the feeling of the hair bundle as very supple; and
"D" means that one or none of the testers evaluated the feeling of the hair bundle as very supple.

Hair Washing Properties 0.8 g of each of the hair fixative foams were applied to a bundle of black virgin hair (length: 15 cm long; weight: 3.0 g), and dried at room temperature to prepare a hair bundle of groomed hair. Then, after bathing the hair bundles for 30 sec in warm water of 40° C., 0.4 g of a 10% shampoo solution was applied and the hair bundles were washed for 30 sec. After that, the hair bundles were again rinsed with 40° C. warm water to wash out the shampoo solution, and amply dried at 50° C., thus obtaining hair bundles for the evaluation of the hair washing properties. These hair bundles were subjected to a sensory test of hair washing properties with ten testers, who evaluated their hair washing properties. The evaluation criteria with regard to the hair washing properties were as follows:

"A" means that the hair washing properties of the hair bundle was evaluated as very good by at least nine testers;
"B" means that the hair washing properties of the hair bundle was evaluated as very good by six to eight testers;
"C" means that the hair washing properties of the hair bundle was evaluated as very good by two to five testers; and
"D" means that the hair washing properties of the hair bundle was evaluated as very good by one or none of the testers.

Touch 0.8 g of each of the hair fixative foams were applied to a bundle of black virgin hair (length: 25 cm long; weight: 5.0 g), and dried at room temperature to prepare a hair bundle for the evaluation of touch. These hair bundles were subjected to a sensory test with ten testers, who evaluated their touch. The evaluation criteria with regard to touch were as follows:

"A" means that the touch of the hair bundle was evaluated as very good by at least nine testers;
"B" means that the touch of the hair bundle was evaluated as very good by six to eight testers;
"C" means that the touch of the hair bundle was evaluated as very good by two to five testers; and
"D" means that the touch of the hair bundle was evaluated as very good by one or none of the testers.

Spreadability of the Hair Fixative

The ten testers judged in a sensory test the spread when applying 0.8 g of each of the hair fixative foams to a bundle of black virgin hair (length: 25 cm long; weight: 5.0 g), and evaluated the spreadability of the hair fixative serving as a hair fixative cosmetic substance. The evaluation criteria with regard to spreadability were as follows:

"A" means that the spread at the time of application was evaluated as very good by at least nine testers;
"B" means that the spread at the time of application was evaluated as very good by six to eight testers;
"C" means that the spread at the time of application was evaluated as very good by two to five testers; and
"D" means that the spread at the time of application evaluated as very good by one or none of the testers.

Storage Stability

The various amphoteric urethane resin aqueous solutions were given into 100 ml transparent glass bottles, and left standing for two weeks at 50° C. Then their external appearance was observed, to evaluate the storage stability of the amphoteric urethane resin aqueous solutions. The evaluation criteria with regard to storage stability were as follows:

"A" means that there was no separation at all of the silicon polymer;
"B" means that there was almost no separation of the silicon polymer; and
"D" means that separation of the silicon polymer was observed.

TABLE 2

| | working examples | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| setting properties | A | A | A | A | A | A | A | A | A | A | A | A |
| texture | A | A | A | A | A | A | A | A | A | A | A | A |
| hair washing properties | B | B | B | B | B | B | B | B | A | A | A | A |
| touch | B | B | B | B | B | B | A | A | B | B | A | A |
| spreadability | A | A | A | A | A | A | A | A | A | A | A | A |
| storage stability | A | A | A | A | A | A | A | A | A | A | A | A |

TABLE 3

| | comparative examples | | | | | | | | |
|---|---|---|---|---|---|---|---|---|---|
| | 1 | 2 | 3 | 4 | 5 | 6 | 7 | 8 | 9 |
| setting properties | A | C | C | C | C | C | C | A | A |
| texture | A | A | A | A | A | A | A | A | A |
| hair washing properties | B | B | B | B | B | B | B | B | B |
| touch | C | B | B | B | B | B | B | A | A |
| spreadability | C | A | A | A | A | A | A | C | C |
| storage stability | — | D | D | D | D | D | D | A | A |

As shown in Table 2, the amphoteric urethane resins of the working examples all have satisfying properties in all categories from the setting properties to storage stability. On the other hand, as shown in Table 3, none of the amphoteric urethane resins of the comparative examples was satisfying with regard to all properties. The amphoteric urethane resin of the Comparative Example 1 does not include a polysiloxane compound, so that its touch and spreadability were poor.

In the amphoteric urethane resins of the Comparative Examples 2 to 7, a polysiloxane compound was added after mixing the reaction product of the second step with water, so that they are type 2 amphoteric urethane resins, and it seems that the polysiloxane compound is not constrained by the backbone of the amphoteric urethane resin, which leads to a poor storage stability. Moreover, as the amphoteric urethane resins of the Comparative Examples 2 to 7 contain a polysiloxane compound that seems not to be constrained by the backbone of the amphoteric urethane resin, the entangling of the molecule chains of the amphoteric urethane resin is impeded, so that the film forming ability decreased and the setting properties were poor. The amphoteric urethane resins of the Comparative Examples 8 and 9, are type 1 amphoteric urethane resins, with polysiloxane chains introduced into the backbone of the amphoteric urethane resin, so that the spreadability of the hair fixative was poor.

Evaluation Used for Hair Fixative Gels

To evaluate the amphoteric urethane resin aqueous solutions of the working examples and the comparative examples obtained as explained above, hair fixative gels of the working examples and the comparative examples were prepared with each of the amphoteric urethane resin aqueous solutions.

That is to say, the components shown in Table 4 were mixed at the proportions shown in that table, and stirred until a viscous gel was formed, thus obtaining the X component for the working examples and comparative examples. Then, the Y component in Table 4 was added to the X component at the proportions shown in that table and mixed until uniform, thus preparing the hair fixative gels according to each of the working examples and comparative examples. These are referred to as the hair fixative gels of the Working Examples 1 to 12 and the hair fixative gels of the Comparative Examples 1 to 9.

The hair fixative gels of the Working Examples 1 to 12 and the hair fixative gels of the Comparative Examples 1 to 9 were evaluated with the same evaluation methods as explained above. Thus, the same results as for the hair fixative foams of the Working Examples 1 to 12 and the hair fixative foams of the Comparative Examples 1 to 9 were obtained.

TABLE 4

| hair fixative gels of working and comp. examples | | weight % |
|---|---|---|
| X component | thicker[b) | 1.5[a) |
| | triethanolamine | 1.1 |
| | ethanol | 10.0 |
| | propylene glycol | 0.5 |
| | 1,3-butylene glycol | 0.5 |
| | deionized water | 50.0 |
| Y component | amphoteric urethane resin aqueous solution of the respective working example or comp. example | 2.5[a) |
| | deionized water | 33.9 |

[a)Dry weight. Weight of residue remaining after heating the solution to 105° C. for three hours.
[b)Structure 2001 ™ by National Starch and Chemical Company.

Evaluation Used for Hair Fixative Aerosol Sprays

To evaluate the amphoteric urethane resin aqueous solutions of the working examples and the comparative examples obtained as explained above, hair fixative aerosol sprays of the working examples and the comparative examples were prepared with each of the amphoteric urethane resin aqueous solutions.

That is to say, the components shown in Table 5 were mixed at the proportions shown in that table, and stirred until uniform, thus obtaining the X component for the working examples and comparative examples. Then, the Y component in Table 5 was added to the X component at the proportions shown in that table, thus preparing hair fixative aerosol sprays according to each of the working examples and comparative examples. These are referred to as the hair fixative aerosol sprays of the Working Examples 1 to 12 and the hair fixative aerosol sprays of the Comparative Examples 1 to 9.

The hair fixative aerosol sprays of the Working Examples 1 to 12 and the hair fixative aerosol sprays of the Comparative Examples 1 to 9 were evaluated with the same evaluation methods as explained above. Thus, the same results as for the hair fixative foams of the Working Examples 1 to 12 and the hair fixative foams of the Comparative Examples 1 to 9 were obtained.

TABLE 5

| hair fixative gels of working and comp. examples | | weight % |
|---|---|---|
| X component | amphoteric urethane resin aqueous solution of the respective working example or comp. example | 2.5[a) |
| | deionized water | 8.0 |
| | dioctyl sodium sulfosuccinate | 0.5 |
| | propylene glycol | 0.1 |
| | 1,3-butylene glycol | 0.3 |
| | ethanol | 48.6 |
| Y component | propellant | 40.0 |

[a)Dry weight. Weight of residue remaining after heating the solution to 105° C. for three hours.

Evaluation Used for Hair Fixative Pump Sprays

To evaluate the amphoteric urethane resin aqueous solutions of the working examples and the comparative examples obtained as explained above, hair fixative pump sprays of the working examples and the comparative examples were prepared with each of the amphoteric urethane resin aqueous solutions by mixing the components listed in Table 6 at the proportion listed in that table and stirring them until uniform.

These are referred to as the hair fixative pump sprays of the Working Examples 1 to 12 and the hair fixative pump sprays of the Comparative Examples 1 to 9.

The hair fixative pump sprays of the Working Examples 1 to 12 and the hair fixative pump sprays of the Comparative Examples 1 to 9 were evaluated with the same evaluation methods as explained above. Thus, the same results as for the hair fixative foams of the Working Examples 1 to 12 and the hair fixative foams of the Comparative Examples 1 to 9 were obtained.

TABLE 6

| hair fixative gels of working and comp. examples | weight % |
|---|---|
| amphoteric urethane resin aqueous solution of the respective working example or comp. example | 2.5[a) |
| deionized water | 85.5 |
| dioctyl sodium sulfosuccinate | 0.5 |
| cetyl alcohol | 0.5 |
| stearyl alcohol | 0.5 |
| propylene glycol | 0.5 |
| ethanol | 10.0 |
| antiseptic | as suitable |

[a)Dry weight. Weight of residue remaining after heating the solution to 105° C. for three hours.

The present invention presents a novel method for manufacturing an amphoteric urethane resin, as well as a novel amphoteric urethane resin made with this manufacturing method. The amphoteric urethane resin can be used advantageously for paints, coating agents, and cosmetics, and particularly advantageously for cosmetics (such as hair fixatives). Using the manufacturing method of the present invention, such an amphoteric urethane resin can be manufactured easily. With the amphoteric urethane resin according to the present invention, at least one effect selected from improving the performance (in the case of hair fixatives, for example hair setting properties, hair texture, hair washing properties, hair touch and spreadability when applying the hair fixative) of paints, coating agents and cosmetics using the amphoteric urethane resin according to the present invention and improving the storage stability of the amphoteric urethane resin compared to conventional amphoteric urethane resins is achieved.

The invention may be embodied in other specific forms without departing from the spirit or essential characteristics thereof. The embodiments disclosed in this application are to be considered in all respects as illustrative and not restrictive, the scope of the invention being indicated by the appended claims rather than by the foregoing description. All changes that come within the meaning and range of equivalency of the claims are intended to be embraced therein.

What is claimed is:

1. A method for manufacturing an amphoteric urethane resin using:
   (A) a polyol compound;
   (B) a polyisocyanate compound;
   (C) a polysiloxane compound (except any having at least one group selected from the group consisting of a hydroxyl group, a primary amino group and a secondary amino group at one or both ends of the siloxane chain);
   (D) a compound having at least one carboxyl group and at least one group selected from the group consisting of a hydroxyl group, a primary amino group and a secondary amino group;
   (E) a compound having at least one tertiary amino group and at least one group selected from the group consisting of a hydroxyl group, a primary amino group and a secondary amino group;

the method comprising:
a first step of manufacturing a prepolymer including isocyanate groups by reacting the compounds (A), (B) and (D) under the condition of excessive isocyanate groups; and
a second step of reacting the prepolymer including the isocyanate groups with the compound (E);
wherein the compound (C) is present in at least one of the first step and the second step.

2. A method for manufacturing an amphoteric urethane resin using:
(A) a polyol compound;
(B) a polyisocyanate compound;
(C) a polysiloxane compound (except any having at least one group selected from the group consisting of a hydroxyl group, a primary amino group and a secondary amino group at one or both ends of the siloxane chain);
(D) a compound having at least one carboxyl group and at least one group selected from the group consisting of a hydroxyl group, a primary amino group and a secondary amino group;
(E) a compound having at least one tertiary amino group and at least one group selected from the group consisting of a hydroxyl group, a primary amino group and a secondary amino group;
the method comprising:
a first step of manufacturing a prepolymer including isocyanate groups by reacting the compounds (A), (B) and (E) under the condition of excessive isocyanate groups; and
a second step of reacting the prepolymer including the isocyanate groups with the compound (D);
wherein the compound (C) is present in at least one of the first step and the second step.

3. The manufacturing method according to claim 1, wherein the weight ratio of the compound (C) to the compounds (A), (B), (D) and (E), (C)/((A)+(B)+(D)+(E)) is 0.1/100 to 30/100.

4. The manufacturing method according to claim 2, wherein the weight ratio of the compound (C) to the compounds (A), (B), (D) and (E), (C)/((A)+(B)+(D)+(E)) is 0.1/100 to 30/100.

5. A method for manufacturing an amphoteric urethane resin using:
(A) a polyol compound;
(B) a polyisocyanate compound;
(C) a polysiloxane compound (except any having at least one group selected from the group consisting of a hydroxyl group, a primary amino group and a secondary amino group at one or both ends of the siloxane chain);
(D) a compound having at least one carboxyl group and at least one group selected from the group consisting of a hydroxyl group, a primary amino group and a secondary amino group;
(E) a compound having at least one tertiary amino group and at least group one selected from the group consisting of a hydroxyl group, a primary amino group and a secondary amino group;
(F) a compound having at least one group selected from the group consisting of a hydroxyl group, a primary amino group and a secondary amino group, and structural units indicated by the following formula (11)

$$—(C_2H_4O)_p(C_3H_6O)_q— \qquad (11)$$

wherein "p" is an integer of 1 to 500, "q" is an integer of 0 to 400, and
wherein, if the structural units in structural formula (11) are copolymers of $C_2H_4O$ and $C_3H_6O$ (that is, q≠0), then they can be random copolymers or block copolymers;
the method comprising:
a first step of manufacturing a prepolymer including isocyanate groups by reacting the compounds (A), (B), (D) and (F) under the condition of excessive isocyanate groups; and
a second step of reacting the prepolymer including the isocyanate groups with the compound (E);
wherein the compound (C) is present in at least one of the first step and the second step.

6. A method for manufacturing an amphoteric urethane resin using:
(A) a polyol compound;
(B) a polyisocyanate compound;
(C) a polysiloxane compound (except any having at least one group selected from the group consisting of a hydroxyl group, a primary amino group and a secondary amino group at one or both ends of the siloxane chain);
(D) a compound having at least one carboxyl group and at least one group selected from the group consisting of a hydroxyl group, a primary amino group and a secondary amino group;
(E) a compound having at least one tertiary amino group and at least one group selected from the group consisting of a hydroxyl group, a primary amino group and a secondary amino group;
(F) a compound having at least one group selected from the group consisting of a hydroxyl group, a primary amino group and a secondary amino group, and structural units indicated by the following formula (11)

$$—(C_2H_4O)_p(C_3H_6O)_q— \qquad (11)$$

wherein "p" is an integer of 1 to 500, "q" is an integer of 0 to 400, and
wherein, if the structural units in structural formula (11) are copolymers of $C_2H_4O$ and $C_3H_6O$ (that is, q≠0), then they can be random copolymers or block copolymers;
the method comprising:
a first step of manufacturing a prepolymer including isocyanate groups by reacting the compounds (A), (B), (E) and (F) under the condition of excessive isocyanate groups; and
a second step of reacting the prepolymer including the isocyanate groups with the compound (D);
wherein the compound (C) is present in at least one of the first step and the second step.

7. The manufacturing method according to claim 5, wherein the weight ratio of the compound (C) to the compounds (A), (B), (D), (E) and (F) (C)/((A)+(B)+(D)+(E)+(F)) is 0.1/100 to 30/100.

8. The manufacturing method according to claim 6, wherein the weight ratio of the compound (C) to the compounds (A), (B), (D), (E) and (F) (C)/((A)+(B)+(D)+(E)+(F)) is 0.1/100 to 30/100.

9. The manufacturing method according to any of claims 1 to 8, wherein, after the second step, a chain-extending reaction is performed by mixing the reaction product of the second step with water.

10. The manufacturing method according to any of claims 1 to 8, wherein, after the second step, a chain-extending reaction is performed by mixing the reaction product of the second step with alkaline water, or a chain-extending reaction is performed by adding an alkaline compound to the reaction product of the second step, and then mixing it with water.

11. The manufacturing method according to any of claims 1 to 8, wherein the compound (C) is at least one selected from the group consisting of polydimethylsiloxane, polyether-modified silicone, cyclic silicone, phenyl-modified silicone, alkyl-modified silicone, and alkoxy-modified silicone.

12. An amphoteric urethane resin obtained by any of the manufacturing methods according to claims 1 to 8.

13. The amphoteric urethane resin according to claim 12, including, in each molecule, carboxylic groups and tertiary amino groups.

14. The amphoteric urethane resin according to claim 13, which forms an aqueous solution obtained by mixing with water.

15. An urethane resin composition comprising the amphoteric urethane resin according to claim 14.

* * * * *